United States Patent [19]
Debs

[11] Patent Number: 5,756,353
[45] Date of Patent: *May 26, 1998

[54] EXPRESSION OF CLONED GENES IN THE LUNG BY AEROSOL-AND LIPOSOME-BASED DELIVERY

[75] Inventor: Robert J. Debs, Mill Valley, Calif.

[73] Assignee: The Regents of the University of California, Oakland, Calif.

[*] Notice: The term of this patent shall not extend beyond the expiration date of Pat. No. 5,641,662.

[21] Appl. No.: 487,793

[22] Filed: Jun. 7, 1995

Related U.S. Application Data

[63] Continuation of Ser. No. 205,822, Mar. 2, 1994, abandoned, which is a continuation of Ser. No. 809,291, Dec. 17, 1991, abandoned.

[51] Int. Cl.$^6$ .................... C12N 15/87; A61K 9/12; A61K 49/00; A61K 9/127
[52] U.S. Cl. .................... 435/375; 435/6; 435/69.1; 435/91.1; 435/172.1; 435/172.3; 435/320.1; 435/377; 424/450; 514/44; 536/24.1; 128/200.14
[58] Field of Search .................... 514/44; 424/450; 435/172.3, 6, 375, 377, 69.1, 91.1, 172.1, 320.1; 935/62, 54, 55, 70, 71; 128/200.14, 200.18, 200.23, 200.24; 536/24.1

[56] References Cited

U.S. PATENT DOCUMENTS

| | | | |
|---|---|---|---|
| 3,826,255 | 7/1974 | Havstad | 128/194 |
| 4,394,448 | 7/1983 | Szoka | 435/172 |
| 4,804,678 | 2/1989 | Augstein | 514/456 |
| 4,946,787 | 8/1990 | Eppstein | 435/240.2 |
| 5,032,407 | 7/1991 | Wagner | 424/520 |
| 5,049,386 | 9/1991 | Eppstein | 524/257 |
| 5,075,229 | 12/1991 | Hanson | 435/172.3 |
| 5,240,842 | 8/1993 | Mets | 435/172.3 |
| 5,240,846 | 8/1993 | Collins | 435/240.1 |
| 5,264,618 | 11/1993 | Felgner et al. | 560/224 |

FOREIGN PATENT DOCUMENTS

| | | |
|---|---|---|
| 0 281 246 A2 | 9/1988 | European Pat. Off. |
| 0 469 632 A1 | 2/1992 | European Pat. Off. |
| 3545126-A | 6/1987 | Germany. |
| 354126 | 8/1931 | United Kingdom. |
| WO 89/02469 | 3/1989 | WIPO. |
| WO 89/12109 | 12/1989 | WIPO. |
| WO 90/12878 | 1/1990 | WIPO. |
| WO 90/01515 | 2/1990 | WIPO. |
| WO 90/06997 | 6/1990 | WIPO. |
| WO 90/10448 | 9/1990 | WIPO. |
| WO 91/15501 | 10/1991 | WIPO. |
| WO 92/05252 | 4/1992 | WIPO. |
| WO 92/05273 | 4/1992 | WIPO. |
| WO 92/19749 | 11/1992 | WIPO. |
| WO 93/04701 | 3/1993 | WIPO. |
| WO 93/12240 | 6/1993 | WIPO. |
| WO 93/24640 | 12/1993 | WIPO. |

OTHER PUBLICATIONS

Dzau, Victor J., et al. (1993) "Gene therapy for cardiovascular disease", *Tibtech* 11:205–210.

Friedmann, Theodore (1989) "Progress Toward Human Gene Therapy", *Science* 244:1275–1281.

Zhu, Ning, et al., (1993) "Systemic Gene Expression After Intravenous DNA Delivery into Adult Mice", *Science*, 261:209–211.

Rosenfeld, et al. (1992) "In vivo Transfer of the Human Cystic Fibrosis Transmembrane Conductance Regulator Gene to the Airway Epithelium", *Cell*, 68:143–155.

Alton, E., et al. (1993) "Non–invasive liposome–mediated gene delivery can correct the ion transport defect in cystic fibrosis mutant mice", *Nature Genetics*, 5:135–142.

Papahadjopoulos, et al., (1975) "Cochleate Lipid Cylinders: Formation by Fusion of Unilamellar Lipid Vesicles," *Biochimica et Biophysica Acta*, 394:483–491.

Deamer, et al., (1976) "Large Volume Liposomes by an Ether Vaporization Method", *Biochimica et Biophysica Acta*, 443:629–634.

Ostro, et al., (1977) "Incorporation of High Molecular Weight RNA into Large Artificial Lipid Vesicles", *Biochemical and Biophysical Research Communications*, 76(3):836–842.

Enoch, et al., (1979) "Formation and Properties of 1000–Å–Diameter, Single–Bilayer Phospholipid Vesicles", *PNAS (USA)*, 76(1):145–149.

Wilson, et al., (1979) "The Introduction of Poliovirus RNA into Cells via Lipid Vesicles (Lipsomes)", *Cell*, 17:77–84.

Fraley, et al., (1979) "Entrapment of a Bacterial Plasmid in Phospholipid Vesicles: Potential for Gene Transfer", *PNAS (USA)*, 76(7):3348–3352.

Leserman, et al., (1980) "Targeting to Cells of Fluorescent Liposomes Covalenty Coupled wth Monoclonal Antibody or Protein A", *Nature*, 288:602–604.

Beaucage, et al., (1981) "Deoxynucleoside Phosphoramidites—A New Class of key Intermediates for Deoxypolynucleotide Synthesis", *Tetrahedron Letters*, 22(20):1859–1862.

Duckworth, et al. (1981) "Rapid Synthesis of Oligodeoxyribonucleotides VI. Efficient, Mechanised Synthesis of Heptadecadeoxyribonucleotides by an Improved Solid Phase Phosphotriester Route", *Nucleic Acids Research*, 9(7):1691–1706.

(List continued on next page.)

*Primary Examiner*—Charles C.P. Rories
*Attorney, Agent, or Firm*—Townsend and Townsend and Crew

[57] ABSTRACT

Methods for the delivery of genes directly to the lungs are disclosed. Liposome-nucleic acid complexes are delivered via aerosol with the subsequent in viva expression of a protein encoded by the delivered gene. The invention provides a convenient method for treating pulmonary disorders, as well as for delivering substances systemically via the lung.

25 Claims, 1 Drawing Sheet

OTHER PUBLICATIONS

Martin, et al. (1981) "Immunospecific Targeting of Liposomes to Cells: A Novel and Efficient Method for Covalent Attachment of Fab' Fragments via Disulfide Bonds", *Biochemistry*, 20:4229–4238.

Matteucci, et al. (1981) "Synthesis of Deoxyoligonucleotides on a Polymer Support," *J. Am. Chem. Soc.*, 103:3185–3191.

Volloch, et al. (1981) "Stability of Globin mRNA in Terminally Differentiating Murine Erythroleukemia Cells," *Cell*, 23:509–514.

Bothwell, et al. (1981) "Heavy Chain Variable Region Contribution to the $NP_b$ Family of Antibodies: Somatic Mutation Evident in a $\gamma$2a Variable Region," *Cell*, 24:625–637.

Edge, et al. (1981) "Total Synthesis of a Human Leukocyte Interferon Gene," *Nature*, 292:756–762.

Schaefer-Ridder, et al. (1981) "Lipsomes as Gene Carriers: Efficient Transformation of Mouse L Cells by Thymidine Kinase Gene," *Science*, 215(8):166–168.

Gorman, et al. (1982) "Recombinant Genomes which Express Chloramphenicol Acetyltransferase in Mammalian Cells," *Molecular and Cellular Biology* 2(2):1044–1051.

Gorman, et al. (1982) "The Rous Sarcoma Virus Long Terminal Repeat is a Strong Promoter when Introduced into a Variety of Eukaryotic Cells by DNA–Mediated Transfection," *PNAS (USA)*, 79:6777–6781.

Long, et al. (1984) "Complete Sequence of the cDNA for Human $\alpha_1$–Antitrypsin and the Gene for the S Variant," *Biochemistry*, 23:4828–4837.

Nambiar, et al. (1984) "Total Synthesis and Cloning of a Gene Coding for the Ribonuclease S. Protein," *Science* 223:1299–1301.

Jay, et al. (1984) "Chemical Synthesis of a Biologically Active Gene for Human Immune Interferon–$\gamma$," *Journal of Biological Chemistry*, 259(10):6311–6317.

Kunkel, Thomas (1985) "Rapid and efficient site–specific mutagenesis without phenotypic selection," *PNAS (USA)*, 82:488–492.

Boshart, et al. (1985) "A very Strong Enhancer is Located Upstream of an Immediate Early Gene of Human Cytomegalovirus," *Cell*, 41:521–530.

Stinski, et al. (1985) "Activation of the Major Immediate Early Gene of Human Cytomegalovirus by cis–Acting Elements in the Promoter–Regulatory Sequence and by Virus–specific trans–acting Components," *Journal of Virology*, 55(2):431–441.

Cullen, B.R. (1986) "Trans–Activation of Human Immunodeficiency Virus Occurs via a Bimodal Mechanism," *Cell*, 46:973–982.

Benvenisty, et al. (1986) "Direct introduction of genes into rats and expression of the genes," *PNAS (USA)*, 83:9551–9555.

Wang, et al. (1987) "pH Sensitive Immunoliposomes Mediate Target–Cell–Specific Delivery and Controlled Expression of a Foreign Gene in a Mouse," *PNAS (USA)*, 84:7851–7855.

Sakai, et al. (1988) "Hormone–Mediated Repression: A Negative Glucocorticoid Response Element from the Bovine Prolactin Gene," *Genes and Development*, 2:1144–1154.

Stamatatos, et al. (1988) "Interactions for Cationic Lipid Vesicles with Negatively Charged Phospholipid Vesicles and Biological Membranes", *Biochemistry*, 27:3917–3925.

Wu, et al. (1988) "Receptor–Mediated Gene Delivery and Expression In Vivo," *J. Biological Chemistry*, 263(29):14621–14624.

Kaneda, et al. (1989) "Increased Expression of DNA Cointroduced with Nuclear Protein in Adult Rat Liver," *Science* 243:375–378.

Rommens, et al. (1989) "Identification of the Cystic Fibrosis Gene: Chromosome Walking and Jumping," *Science*, 245:1059–1065.

Goodfellow, P.N. (1989) "Steady Steps Lead to the Gene," *Nature*, 341:102–103.

Mizuno, et al. (1989) "In Vitro and In Vivo Expression of Human Interferon–$\beta$ in Glioma Cells Transfected with its Gene Encapsulated in Liposomes," *J. Interferon Research*, 9, Supp. 2:S151 (Abstract Al–8).

Huang, et al. (1990) "Intervening Sequences Increase Efficiency of RNA 3'Processing and Accumulation of Cytoplasmic RNA," *Nucleic Acids Research*, 18(4):937–947.

Ono, et al. (1990) "Plasmid DNAs Directly Injected into Mouse Brain with Lipofectin Can Be Incorporated and Expressed by Brain Cells," *Neuroscience Letters*, 117:259–263.

Holt, et al. (1990) "Lipofection of cDNAs in the Embryonic Vertebrate Central Nervous System," *Neuron*, 4:203–214.

Uhlman, et al. (1990) "Antisense Oligonucleotides: A New Therapeutic Principle," *Chemical Reviews*, 90(4):543–584.

Crystal, R.G. (1990) "$\alpha$1–Antitrypsin Deficiency, Emphysema, and Liver Disease", *The Journal of Clinical Investigation, Inc.*, 85:1343–1352.

Shyu, Ann–Bin, et al. (1989) "The c–fos transcript is targeted for rapid decay by two distinct mRNA degradation pathways", *Genes & Development*, 3:60–72.

Rosenberg, et al. (1990) "Gene Transfer into Humans— Immunotherapy of Patients with Advanced Melanoma, Using Tumor–Infiltrating Lymphocytes Modified by Retroviral Gene Transduction", *The New England Journal of Medicine*, 323(9):570–578.

Burhans, et al. (1990) "Identification of an Origin of Bidirectional DNA Replication in Mammalian Chromosomes", *Cell*, 62:955–965.

Verma (1990) "Gene Therapy: Treatment of disease by introducing healthy genes into the body is becoming feasible. But the therapy will not reach its full potential until the genes can be coaxed to work throughout life", *Scientific American*, 68–84.

Barr, et al. (1991) "Expression of Recombinant Genes in Myocardium In Vivo Following Direct Injection of DNA", *Clinical Research*, 39:2:152A.

Kitsis, et al. (1991) "Behaviour of Genes Directly Transferred to Rat Heart In Vivo", *Clinical Research*, 39:2:152A.

Palmiter, et al. (1991) "Heterologous introns can enhance expression of transgenes in mice", *PNAS (USA)*, 88:478–482.

Felgner, et al. (1991) "Gene Therapeutics", *Nature*, 349:351–352.

Weatherall, D.J. (1991) "Gene Therapy in Perspective", *Nature*, 349:275–276.

Fleischman, Roger A. (1991) Southwestern Internal Medicine Conference: Human Gene Therapy, *The American Journal of the Medical Sciences*, 301(5):353–363.

Kitsis, et al. (1991) "Hormonal Modulation of a Gene Injected into Rat Heart In Vivo", *PNAS (USA)*, 88:4138–4142.

Choi, et al. (1991) "A Generic Intron Increases Gene Expression in Transgenic Mice", *Molecular and Cellular Biology*, 11(6):3070–3074.

Lim, et al. (1991) "Direct In Vivo Gene Transfer into the Coronary and Peripheral Vasculatures of the Intact Dog", *Circulation*, 83(6):2007–2001.

Wu, et al. (1991) "Receptor–Mediated Gene Delivery In Vivo", *Journal of Biological Chemistry*, 266(22):14338–14342.

Acsadi, et al. (1991) "Human Dystrophin Expression in mdx Mice after Intramuscular Injection of DNA Constructs", *Nature*, 352:815–818.

Rosenberg (1991) "Immunotherapy and Gene Therapy of Cancer", *Cancer Research (Supp.)*, 51(18):5074S–5079S.

Anderson, W. French (1992) "Human Gene Therapy", *Science* 256:808–813.

Collins, Francis S. (1992) "Cystic Fibrosis: Molecular Biology and Therapeutic Implications", *Science*, 256:774–783.

Cox, et al. (1988) "Emphysema of Early Onset Associated with a Complete Deficiency of Alpha–1–Antitrypsin (null homozygotes)[1–3]",*Am. Rev. Respir. Dis.*, 137:371–375.

Maram, et al. (1980) "Sequencing End–Labeled DNA with Base–Specific Chemical Cleavages", *Methods in Enzymology*, 65:499–560.

Wright, B.M. (1958) "A New Nebuliser", *Lancet*, 2:24–25.

Raabe, Otto G. (1971) "Particle Size Analysis Utilizing Group Data and the Log–Normal Distribution", *J. Aerosol Sci.*, 2:289–303.

Szoka, et al. (1978) "Procedure for preparation of liposomes with large internal aqueous space and high capture by reverse–phase evaporation", *PNAS (USA)*, 75(9):4194–4198.

Dobbs, et al. (1986) "An improved method for isolating Type II cells in High Yield and Purity[1–3]", *Amer. Rev. Respiratory Disease*, 134:141–145.

Debs, et al. (1986) "Selective Enhancement of Pentamidine Uptake in the Lung by Aerosolization and Delivery in Liposomes", *Amer. Rev. Respiratory Disease*, 135:731–737.

Lai, et al. (1988) "The essential role of microsomal deacetylase activity in the metabolic activation, DNA–(deoxyguanosin–8–yl)–2–aminofluorene adduct formation and initiation of liver tumors by N–hydroxy–2–acetylaminoflurorene in the livers of infant male B6C3F$_1$ mice", *Carcinogenesis*, 9:1295–1302.

Beardsley, et al. (1989) "Winning Candidate: A painstaking search identifies the gene for cystic fibrosis", *Sci. Am.*, 261:28–30.

Treat, et al. (1990) "Antitumor activity of liposome–encapsulated doxorubicin in advanced breast cancer Phase II study", *J. Natl. Cancer Instit.*, 82:1706.

Rasmussen, O.F. (1991) "Listeria monocytogenes can be classified into two major types according to the sequence of the listeriolysin gene", *Infect. and Immun.*, 59(11):3945–3951.

Marino, et al. (1991) "Localization of the Cystic Fibrosis Transmembrane Conductance Regulator in Pancreas", *J. Clin. Invest.*, 88:712–716.

Chou, et al. (1991) "Characterization of the Promoter Region of the Cystic Fibrosis Transmembrance Conductance Regulator Gene", *The Journal of Biological Chemistry*, 266:24471–24476.

Trezise, et al. (1991) "In Vivo Cell–Specific Expression of the Cystic Fibrosis Transmembrane Conductance Regulator," *Nature*, 353:434–437.

Brinster, et al. (1988) "Introns Increase Transriptional Efficiency in Transgenic Mice", *Proc. Natl. Acad. Sci. USA*, 85:836–840.

Debs, et al. (1992) "Prolonged Transgene Expression in Rodent Lung Cells", *Am. J. Respir. Cell Mol. Biol.*, 7:406–413.

Drumm, et al. (1990) "Correction of the Cystic Fibrosis Defect In Vitro by Retrovirus–Mediated Gene Transfer", *Cell*, 62:1227–1233.

Gregory, et al. (1990) "Expression and Characterization of the Cystic Fibrosis Transmembrane Conductance Regulator," *Nature*, 347:382–386.

Nicolau, et al. (1983) "In Vivo Expression of Rat Insulin After Intravenous Administration of the Liposome–Entrapped Gene for Rat Insulin I", *Proc. Natl. Acad. Sci. USA*, 80:1068–1072.

Rich, et al. (1990) "Expression of Cystic Fibrosis Transmembrane Conductance Regulator Corrects Defective Chloride Channel Regulation in Cystic Fibrosis Airway Epithelial Cells", *Nature*, 347:358–363.

Riordan, et al. (1989) "Identification of the Cystic Fibrosis Gene: Cloning and Characterization of Complementary DNA", *Science*, 245:1066–1073.

Stribling, et al. (1992) "The Mouse as a Model for Cationic Lipsome–Based Aerosolized Gene Delivery", *Journal of Biopharmaceutical Sciences*, 3(1/2) 255–263.

Taylor, et al. (1993) "Liposomes for Drug Delivery to the Respiratory Tract", *Drug Development and Industrial Pharmacy*, 19(1/2), 123–142.

K. Brigham et al. Am. J. Med. Sci. ('89) 298(4) 278–81.

P. Felgner et al. PNAS ('87) 84: 7413–17.

H. San et al. Hum. Gene Therapy ('93) 4: 781–788.

L. Schwarz et al. Hum. Gene Therapy ('96) 7: 731–41.

R. Stribling et al. PNAS ('92) 89: 11277–81.

X. Gao et al. BBRC ('91) 179: 280–285.

K. Yoshinura et al. NAR ('92) 20(12) 3233–40.

S. Hyde et al. Nature ('93) 362: 250–5.

D. Porteous et al. Tibtech ('93) 11: 173–181.

J. Van Brunt Biotechnology ('88) 6(10): 1149–54.

A. Dusty Miller Nature ('92) 357: 455–60.

N. Dillon Tibtech ('93) 11: 167–73.

EXPRESSION OF CLONED GENES IN THE LUNG BY AEROSOL-AND LIPOSOME-BASED DELIVERY

CROSS REFERENCE TO RELATED APPLICATIONS

This application is a continuation of U.S. application Ser. No. 08/205,822, filed Mar. 2, 1994, now abandoned, which is a continuation of U.S. application Ser. No. 08/809,291 filed Dec. 17, 1991 (now abandoned).

DESCRIPTION

1. Technical Field

The present invention relates generally to the field of gene therapy. More particularly, the instant invention pertains to a method of delivering nucleic acids to the lungs for the in vivo expression of the same.

2. Background of the Invention

Gene therapy provides a means for transfer of a desired gene into a subject with the subsequent in vivo expression thereof. Gene transfer can be accomplished by transfecting the subject's cells or tissues ex vivo and reintroducing the transformed material into the host. Alternatively, genes can be administered directly to the recipient.

Hazinski et al., *Am. J. Respir. Cell Mol. Biol.* (1991) 4:206–209, relates to liposome-mediated gene transfer of DNA into the intact rodent lung. Three fusion gene constructs were complexed to cationic liposomes—1) the chloramphenicol acetyltransferase ("CAT") gene linked to a Rous sarcoma virus ("RSV") promoter; 2) the CAT gene linked to a mouse mammary tumor virus ("MMTV") promoter; and 3) a cytomegalovirus-β-galactosidase ("CMV-β-gal") fusion gene. The liposome/DNA complexes were instilled into the cervical trachea of rats and detectable levels of gene expression observed.

Brigham et al., *Am. J. Med. Sci.* (1989) 298:278–281, describes the in vivo transfection of murine lungs with the CAT gene using a liposome vehicle. Transfection was accomplished by intravenous, intratracheal or intraperitoneal injection. Both intravenous and intratracheal administration resulted in the expression of the CAT gene in the lungs. However, intraperitoneal administration did not.

Canonico et al., *Clin. Res.* (1991) 39:219A describes the expression of the human α-1 antitrypsin gene, driven by the CMV promoter, in cultured bovine lung epithelial cells. The gene was added to cells in culture using cationic liposomes. The experimenters also detected the presence of α-1 antitrypsin in histological sections of the lung of New Zealand white rabbits following the intravenous delivery of gene constructs complexed to liposomes.

Wolff et al., *Science* (1990) 247:1465–1468 relates to direct transfer of the CAT, β-gal and luciferase genes into mouse skeletal muscle in vivo. Gene expression was observed in all three cases.

Nabel et al., *Science* (1990) 249:1285–1288, pertains to in vivo intra-arterial transfection of pigs with liposomes containing a β-gal expression plasmid. Site-specific gene expression was observed in the arterial wall.

None of the above cited art, however, suggests the use of aerosol administration to deliver genes directly to the lung. Such a mode of administration allows the direct delivery of therapeutic agents to pulmonary tissues. PCT Application PCT/US90/01515, having International Publication No. WO 90/11092, describes a method for introducing naked DNA into muscle tissue. Although the application suggests that lung disorders might be treated in vivo by the introduction of DNA thereto, no detailed description of how aerosol delivery might be accomplished is given. Aerosol delivery provides a number of advantages over other modes of administration. For example, aerosol administration can serve to reduce host toxicity. Such an effect has been observed with the delivery of substances such as pentamidine and cytokines, which can be highly toxic when delivered systemically, but well tolerated when aerosolized. See, e.g., Debs et al., *Antimicrob. Agents Chemother.* (1987) 31:37–41; Debs et al., *Amer. Rev. Respir. Dis.* (1987) 135:731–737; Debs et al., *J. Immunol.* (1988) 140:3482–3488; Montgomery et al., *Lancet* (1987) 11:480–483; Montgomery et al., *Chest* (1989) 95:747–751; Leoung et al., *N. Eng. J. Med.* (1990) 323:769–775. Additionally, rapid clearance of circulating liposomes by the liver and spleen reticuloendothelial system can be reduced thereby allowing the sustained presence of the administered substance. Serum induced inactivation of the therapeutic agent is also reduced.

SUMMARY OF THE INVENTION

The instant invention is based on the surprising discovery that genes can be directly delivered to the lungs and, subsequently expressed therein, by aerosol administration. The ability to express cloned genes in the lung after aerosol delivery allows the use of gene therapy approaches to treat and/or prevent a wide variety of pulmonary disorders.

Accordingly, in one embodiment, the subject invention is directed to a method of delivering a liposome-nucleic acid complex to a mammalian subject for the in vivo expression of a polypeptide encoded by the nucleic acid. The method comprises (a) providing a liposome-nucleic acid aerosol wherein the nucleic acid is under the control of regulatory elements permitting the in vivo expression of a polypeptide encoded therein; and (b) administering an effective amount of the aerosol under conditions whereby the aerosol is delivered to the subject's alveoli.

In another embodiment, the invention is directed to a method, as above, wherein the aerosol is delivered to the subject's proximal and/or distal airways.

In particularly preferred embodiments, the nucleic acid used is DNA and the liposome is a cationic liposome.

These and other embodiments of the present invention will readily occur to those of ordinary skill in the art in view of the disclosure herein.

DETAILED DESCRIPTION

Figure 1:
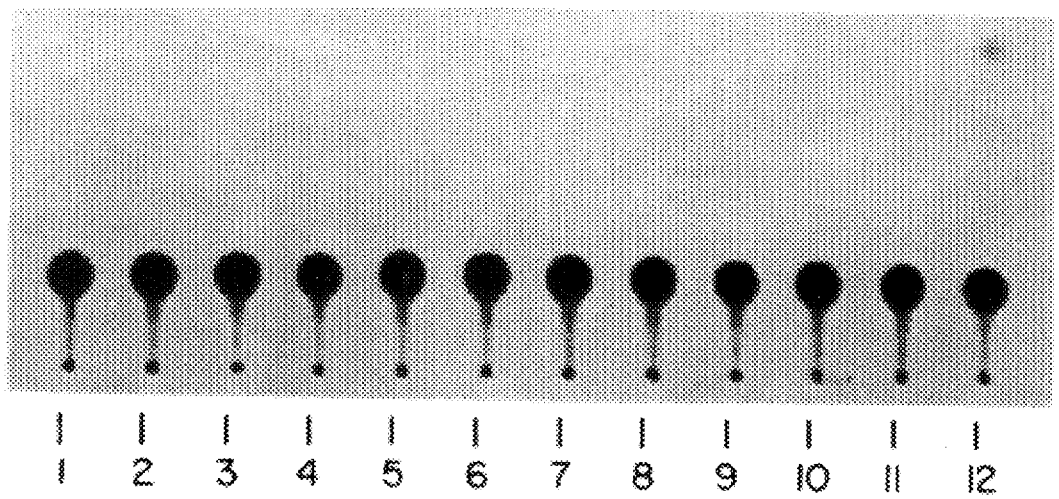
FIG. 1 depicts the results of an experiment wherein mice were administered pRSV-CAT complexed to DOTMA-containing liposomes. Lanes 1–3 were derived from mice receiving no treatment; lanes 4–6 represent mice administered 0.5 mg pRSV-CAT with 1.0 μmole DOTMA-cholesterol; lanes 7–9 were derived from mice receiving 2.0 mg pRSV-CAT alone; and lanes 10–12 represent mice given 2.0 mg pRSV-CAT with 4.0 μmol DOTMA-cholesterol in a 2 to 1 molar ratio.

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Sambrook, et al., Molecular Cloning: A Laboratory Manual, Second Edition (1989) Vols. 1–3; DNA Cloning (1985) Vols. I and II, D. N. Glover (ed.); Nucleic Acid Hybridization (1984), B. D. Hames, et al. (eds.); Perbal, B., A Practical Guide to Molecular Cloning (1984); Methods in Enzymology (the series), Academic Press, Inc.; Vectors: A Survey of Molecular Cloning Vectors and Their Uses (1987), R. L. Rodriguez, et al., (eds.), Butterworths; and Miller, J. H., et al., Experiments in Molecular Genetics (1972) Cold Spring Harbor Laboratory.

All patents, patent applications, and publications mentioned herein, whether supra or infra, are hereby incorporated by reference.

A. Definitions

In describing the present invention, the following terms will be employed, and are intended to be defined as indicated below.

By "mammalian subject" is meant any member of the class Mammalia, including humans and all other mammary gland possessing animals (both male and female), such as cats, dogs, rodents, ruminants, including, but not limited to, bovine, porcine and Ovis (sheep and goats) species, and other domestic animals and pets.

A "replicon" is any genetic element (e.g., plasmid, chromosome, virus) that functions as an autonomous unit of nucleic acid replication in vivo; i.e., capable of replication under its own control.

A "vector" is a replicon, such as a plasmid, phage, or cosmid, to which another nucleic acid segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A "coding sequence" is a nucleic acid sequence which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus.

A "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

Nucleic acid "control sequences" or "regulatory elements" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous nucleic acid sequence.

A cell has been "transformed" by exogenous nucleic acid when such exogenous nucleic acid has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a nucleic acid construct is an identifiable segment of nucleic acid within or attached to another nucleic acid molecule that is not found in association with the other molecule in nature. Thus, when the heterologous region encodes a eucaryotic gene, the gene will usually be flanked by sequences that do not flank the eucaryotic gene in the nature. Another example of a heterologous coding sequence is a construct where the coding sequence itself is not found in nature (e.g., synthetic sequences having codons different from the native gene). Allelic variation or naturally occurring mutational events do not give rise to a heterologous region of nucleic acid, as used herein.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

An "isolated" polypeptide or nucleic acid sequence is one which is devoid of other substances (either in whole or part) with which the polypeptide or antibody would be associated in its natural environment.

By "liposome-nucleic acid complex" is meant a nucleic acid sequence as described above, either bound to the surface of, or entrapped in, a liposome preparation, as discussed below. The liposome preparation can also contain other substances, such as enzymes necessary for transcription and translation, cofactors, etc. Furthermore, the liposome-nucleic acid complex can include targeting agents to deliver the complex to particular cell or tissue types. Such agents are discussed further below.

An "effective amount" of the aerosolized liposome-nucleic acid preparation, is a dose sufficient to effect treatment, that is, to cause alleviation or reduction of symptoms, to inhibit the worsening of symptoms, to prevent the onset of symptoms, and the like. The dosages of the present compositions which will constitute an effective amount can be determined in view of this disclosure by one of ordinary skill in the art by running routine trials with appropriate controls. Comparison of the appropriate treatment groups to the controls will indicate whether a particular dosage is effective in preventing or reducing particular symptoms. Appropriate doses are discussed further below.

B. General Methods

Central to the present invention is the discovery that genes can be delivered to the lung, and subsequently expressed in vivo, via aerosol administration. The instant invention takes advantage of the use of liposomes as a delivery mechanism. Liposomes are able to stably bind or entrap and retain nucleic acid and permit a system amenable to nebulization, whereby intact genes can be delivered to specific pulmonary tissues. Particular sites in the lung are targeted by varying the size of the aerosol particles administered, as discussed more fully below. Targeting agents, such as antibodies directed against surface antigens expressed on specific lung cell types, can also be covalently conjugated to the liposomal surface so that nucleic acid can be delivered to specific tissues and cells. Liposomes also allow for the delivery of relatively large amounts of nucleic acid, without a toxic effect, such that therapeutically effective amounts of the desired protein can be expressed in vivo. For a review of the use of liposomes as carriers for delivery of nucleic acids, see, Hug and Sleight, *Biochim. Biophys. Acta.* (1991) 1097:1–17; Straubinger et al., in Methods of Enzymology (1983), Vol. 101, pp. 512–527.

Nucleic acid sequences, including both coding and regulatory sequences, are used in the liposomal preparation. The desired gene or genes are conveniently added to the liposomal preparation via vectors which include the necessary elements to direct transcription and translation in a host cell. If expression is desired using the host's enzymes (such as by the use of endogenous RNA polymerase), the gene or genes will be present in the liposomes, operatively linked to regulatory sequences recognized by the particular host, or even particular cells within the host. Thus, eucaryotic and phage regulatory elements will generally be present for expression in mammalian hosts. Such regulatory sequences are known in the art and are discussed more fully below. However, liposomal preparations can also be formulated that include the necessary enzymes for transcription and translation, or sequences (i.e. DNA or mRNA), encoding these enzymes. Accordingly, vectors can be constructed utilizing procaryotic, eucaryotic, or phage control elements, and compatible enzymes also entrapped, such that transcription and translation can be directed by exogenous enzymes.

The present invention is particularly useful for the delivery of substances directly into the lung for the prevention and/or treatment of pulmonary disorders such as lung cancer, emphysema, asthma, lung infections such as chronic bronchitis and pneumonia, degenerative diseases of the lung, as well as genetic disorders such as cystic fibrosis and α-1 antitrypsin deficiency.

For the treatment of lung tumors, genes encoding toxic peptides (i.e. chemotherapeutic agents such as ricin, diphtheria toxin and cobra venom factor), tumor suppressor genes such as p53, genes coding for mRNA sequences which are antisense to transforming oncogenes, or other antineoplastic peptides, such as tumor necrosis factor (TNF) and other cytokines, or transdominant negative mutants of transforming oncogenes, can be delivered for expression at or near the tumor site. It has been shown that TNF-α is not structurally altered and retains full biologic activity following nebulization. Debs, et al., *J. Immunol.* (1988) 140:3482–3488. Such tumors can be specifically targeted by incorporating targeting agents, such as antibodies directed against tumor cell surface antigens, onto the liposomal surface. See, e.g., Leserman, et al., *Nature* (1980) 288:602–604; Huang, et al., *J. Biol. Chem.* (1980) 255:8015–8018; Martin, et al., *Biochemistry* (1981) 20:4229–4238, for methods of incorporating antibodies onto liposomal surfaces.

Similarly, genes coding for peptides known to display antiviral and/or antibacterial activity, or stimulate the host's immune system, can also be administered to the lung in order to treat pulmonary infections. Thus, the genes encoding many of the various cytokines (or functional fragments thereof), such as the interleukins, interferons, and colony stimulating factors, will find use with the instant invention. The gene sequences for a number of these substances are known. It has been found that recombinant interferon-γ, when administered by aerosol, retains its activity and displays little or no toxicity in mammals. Debs, et al., *J. Immunol.* (1988) 140:3482–3488. Furthermore, aerosolized interferon-γ produces significant anti-pneumocystis carinii pneumonial (PCP) activity in immunodeficient mice with PCP. Beck et al., *Infect. and Immun.* (1991)

Genes encoding antioxidants will also find use for the treatment or prevention of lung damage due to degenerative lung disorders caused by smoking and other environmental agents. For example, genes encoding superoxide dismutase (SOD) or catalase, as well as α-1 antitrypsin, will be particularly useful for this purpose. These gene sequences are known. See, e.g., Long et al., *Biochem.* (1984) 23:4828–4837 for the α-1 antitrypsin gene sequence.

For the treatment of genetic disorders, such as cystic fibrosis and emphysema, functional genes, corresponding to genes known to be deficient in the particular disorder, can be administered to the subject. For example, it is known that individuals lacking sufficient levels of α-1 antitrypsin are prone to emphysema and other pulmonary disorders. Thus, this gene can be administered prophylactically, as well as in response to clinical manifestations of the disease, for both the prevention and/or treatment of this disorder. Similarly, the gene involved in cystic fibrosis has been identified. Goodfellow, P., *Nature* (1989) 341:102–103; Rommens, et al., *Science* (1989) 245:1059–1065; Beardsley, et al., *Sci. Am.* (1989) 261:28–30. Thus, this gene, or functional fragments thereof, can be delivered to subjects in order to treat this disorder.

The invention also finds use for the delivery of substances into the systemic circulation via the lung. For example, as explained above, a number of substances, such as cytokines, are toxic when administered using conventional methods of delivery. See, e.g. Debs et al., *J. Immunol.* (1988) 140:3482–3488. The invention allows the delivery of these substances, i.e. in order to fight cancer, as well as bacterial and viral infection, systemically. This approach has already shown promise for the treatment of extra-pulmonary cancer in humans.

The instant methods will also find use in antisense therapy, for the delivery of oligonucleotides able to hybridize to specific complementary sequences, thereby inhibiting the transcription and/or translation of these sequences. Thus, DNA or RNA coding for proteins necessary for the progress of a particular disease, can be targeted, thereby disrupting the disease process. For a review of antisense therapy and oligonucleotides useful in the same, see, Uhlmann, E. and Peyman, A., *Chem. Rev.* (1990) 90:543–584.

Isolation of Genes and Construction of Vectors

Nucleic acid sequences, for use in the present invention, can be derived from known sources, i.e., by isolating the same from cells containing the desired gene, using standard techniques. Similarly, the gene sequence can be generated synthetically, using standard modes of polynucleotide synthesis, well known in the art. See, e.g. Edge, M. D., *Nature* (1981) 292:756; Nambair, et al, *Science* (1984) 223:1299; Jay, Ernest, *J Biol Chem* (1984) 259:6311. Generally, synthetic oligonucleotides are prepared by either the phosphotriester method as described by Edge et al, *Nature* (supra) and Duckworth et al, *Nucleic Acids Res* (1981) 2:1691, or the phosphoramidite method as described by Beaucage, S. L., and Caruthers, M. H., *Tet. Letts.* (1981) 22:1859, and Matteucci, M. D., and Caruthers, M. H., *J. Am. Chem. Soc.* (1981) 103:3185, and can be prepared using commercially available automated oligonucleotide synthesizers. The gene sequence can be designed with the appropriate codons for the particular amino acid sequence. In general, one will select preferred codons for expression in the intended host. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

A particularly convenient method for obtaining nucleic acid for use in the liposome-nucleic acid preparations, is by recombinant means. Thus, the desired gene can be excised from a plasmid carrying the same, using standard restriction enzymes and procedures. Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in *Methods in Enzymology* (1950) 65:499–560.

Restriction cleaved fragments may be blunt ended by treating with the large fragment of *E. coli* DNA polymerase I (Klenow) in the presence of the four deoxynucleotide triphosphates (dNTPs) using standard techniques. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture can be extracted with e.g. phenol/chloroform, and ethanol precipitated. Treatment under appropriate conditions with S1 nuclease or BAL-31 results in hydrolysis of any single-stranded portion.

Once coding sequences for the desired proteins have been prepared or isolated, they can be cloned into any suitable vector or replicon. Numerous cloning vectors are known to those of skill in the art, and the selection of an appropriate cloning vector is a matter of choice. Ligations to other sequences are performed using standard procedures, known in the art. For example, ligations can be accomplished in 20 mM Tris-Cl pH 7.5, 10 mM MgCl$_2$, 10 mM DTT, 33 ug/ml BSA, 10 mM–50 mM NaCl, and either 40 uM ATP, 0.01–0.02 (Weiss) units T4 DNA ligase at 0° C. (for "sticky end" ligation) or 1 mM ATP, 0.3–0.6 (weiss) units T4 DNA ligase at 14° C. (for "blunt end" ligation). Intermolecular "sticky end" ligations are usually performed at 30–100 ug/ml total DNA concentrations (5–100 nM total end concentration).

The gene can be placed under the control of a promoter, ribosome binding site and, optionally, an operator (collectively referred to herein as "control" elements), so that the gene sequence encoding the desired protein is transcribed into RNA in the host tissue transformed by a vector containing this expression construct. The coding sequence may or may not contain a signal peptide or leader sequence.

As explained above, the choice of regulatory elements will depend on the host being transformed and the type of liposomal preparation used. Thus, if the host's endogenous transcription and translation machinery will be used to express the proteins, control elements compatible with the particular host will be utilized. Several promoters for use in mammalian systems are known in the art and include, but are not limited to promoters derived from SV40, CMV, HSV, RSV, MMTV, T7, T3, among others. Particularly useful in the present invention is the RSV promoter, as described in the examples. Similarly, promoters useful with procaryotic enzymes are known and include the tac, spa, trp, trp-lac λ-p$_L$, T7, phoA, as well as others.

In addition to control sequences, it may be desirable to add regulatory sequences which allow for regulation of the expression of the protein sequences. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

In some cases, it may be desirable to add sequences which cause the secretion of the polypeptide from the host cell, with subsequent cleavage of the secretory signal. It may also be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

If the gene sequence of the desired protein is not known, it can be obtained using the following general technique. The desired protein can be isolated from, for example, tissue samples containing the same. This is generally accomplished by first preparing a crude extract which lacks tissue components and several extraneous proteins. The desired proteins can then be further purified i.e. by column chromatography, HPLC, immunoadsorbent techniques or other conventional methods well known in the art.

Purification of the protein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning:* Vol. I, supra; *Nucleic Acid Hybridization*, supra; *Oligonucleotide Synthesis*, supra; Sambrook, et al., supra.

First, a DNA library is prepared. The library can consist of a genomic DNA library from the species of choice. Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein. The desired DNA sequence can then be cloned into a cloning vector and further used, as described above.

Preparation of Liposomes

Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid, resulting in a liposome-nucleic acid complex which will withstand nebulization. Cationic liposomes have been shown to mediate intracellular delivery of plasmid DNA (Felgner, et al., *Proc. Natl. Acad. Sci.* USA (1987) 84:7413–7416); mRNA (Malone, et al., *Proc. Natl. Acad. Sci.* USA (1989) 86:6077–6081); and purified transcription factors (Debs, et al., *J. Biol. Chem.* (1990) 265:10189–10192), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner, et al., *Proc. Natl Acad. Sci.* USA (1987) 84:7413–7416). Other commercially available liposomes include transfectace (DDAB/DOPE) and DOTAP/DOPE (Boerhinger). Other cationic liposomes can be prepared from readily available materials using techniques well known in the art. See, e.g. PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., in Methods of Immunology (1983), Vol. 101, pp. 512–527. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos, et al., *Biochim. Biophys. Acta* (1975) 394:483; Wilson, et al., *Cell* (1979) 17:77); ether injection (Deamer, D. and Bangham, A., *Biochim. Biophys. Acta* (1976) 443:629; Ostro, et al., *Biochem. Biophys. Res. Commun.* (1977) 76:836; Fraley, et al., *Proc. Natl. Acad. Sci.* USA (1979) 76:3348); detergent dialysis (Enoch, H. and Strittmatter, P., *Proc. Natl. Acad. Sci.* USA (1979) 76:145); and reverse-phase evaporation (REV) (Fraley, et al., *J. Biol. Chem.* (1980) 255:10431; Szoka, F. and Papahadjopoulos, D., *Proc. Natl. Acad. Sci.* USA (1978) 75:145; Schaefer-Ridder, et al., *Science* (1982) 215:166).

The ratio of DNA to liposome is important as this ratio affects the success of nebulization of the liposome complex. Generally, the ratio of DNA to liposomes will be around 1:1 (mg DNA:micromoles lipid). However, this ratio can be varied.

Administration

Following formation, the liposome-nucleic acid complex is made into a solution or suspension for aerosolization, using a pharmaceutically acceptable excipient. Suitable excipients will be those that neither cause irritation to the pulmonary tissues nor significantly disturb ciliary function. Excipients such as water, aqueous saline (with or without buffer), dextrose and water, or other known substances, can be employed with the subject invention. The exact concentration and volume of the solution are not critical, acceptable formulations being readily determined by those of ordinary skill in the art. The concentration and volume of the solution will generally be dictated by the particular nebulizer selected to deliver the complex, and, the intended dose. It is preferred to minimize the total volume, however, to prevent unduly long inhalation times for the subject.

Great care must be taken to prevent macroscopic aggregation of the liposome-nucleic acid complexes, either upon mixing or when they are being aerosolized in the nebulizer. The development of these aggregates results in the formation of large particles which will generally not be aerosolized by the nebulizer and which are too large to penetrate beyond the large airways. Aggregation of the liposome-nucleic acid complex is prevented by controlling the ratio of DNA to liposome (as described above), minimizing the overall concentration in solution, usually less than 5 mg DNA/8 ml solution, and the avoidance of chelating agents such as EDTA, which tend to promote macroaggregation.

The liposome-nucleic acid complex is aerosolized by any appropriate method. Usually, the aerosol will be generated by a medical nebulizer system which delivers the aerosol through a mouthpiece, facemask, etc. from which the subject can draw the aerosol into the lungs. Various nebulizers are known in the art and can be used in the method of the present invention. See, e.g., Boiarski et al, U.S. Pat. No. 4,268,460; Lehmbeck et al, U.S. Pat. No. 4,253,468; U.S. Pat. No. 4,046,146; Havstad et al, U.S. Pat. No. 3,826,255; Knight et al, U.S. Pat. No. 4,649,911; Bordoni et al, U.S. Pat. No. 4,510,929.

The selection of a nebulizer system will depend on whether alveolar or airway delivery (i.e., trachea, pharynx, bronchi, etc.), is desired. A convenient way to insure effective delivery of the nucleic acid to the alveoli is to select a nebulizer which produces sufficiently small particles (e.g., producing particles with a mean particle diameter of less than about 5.0 microns (μm), more preferably having a mean particle diameter of about 0.2 to about 4.0 μm, and most preferably having a mean diameter of about 0.2 to about 2 μm), since the larger particles are generally deposited in the airways (both distal and proximal) or nasopharynx.

As an alternative to selecting small mean particle diameters to achieve substantial alveoli deposition, a very high dosage of the liposome-nucleic acid preparation can be administered, with a larger mean particle diameter. A proviso to such an approach is that the particular liposome-nucleic acid complex is not too irritating at the required dosage and that there are a sufficient number of particles in the total population having a diameter in the 0.5 to about 5 μm range to allow for deposition in the alveoli.

For airway delivery, the mean particle size will be larger. For example, suitable mean particle diameters will generally be less than about 15 μm, more preferably from about 4 μm to about 12 μm, and most preferably from about 5 μm to about 10 μm.

Examples of nebulizers useful for alveolar delivery include the Acorn 1 nebulizer, and the Respirgard II® Nebulizer System, both available commercially from Marquest Medical Products, Inc., Inglewood, Colo. Other commercially available nebulizers for use with the instant invention include the UltraVent® nebulizer available from Mallinckrodt, Inc. (Maryland Heights, Mo.); the Wright nebulizer (Wright, B. M., Lancet (1958) 3:24–25); and the DeVilbiss nebulizer (Mercer et al., *Am. Ind. Hyg. Assoc. J.* (1968) 29:66–78; T. T. Mercer, *Chest* (1981) 80:6(Sup) 813–817). Nebulizers useful for airway delivery include those typically used in the treatment of asthma. Such nebulizers are also commercially available.

One of skill in the art can determine the usefulness of a particular nebulizer by measuring the mean particle size generated thereby with e.g. a 7 stage Mercer cascade impactor (Intox Products, Albuquerque, N.M.). Concentrations of the liposome-nucleic acid complex from the impactor plates can be determined by eluting the complex therefrom and assessing the optical density at an appropriate wavelength and comparing to standard curves. Results are generally expressed as mass median aerodynamic diameter±geometric standard deviation (Raabe, *J. Aerosol Sci.* (1971) 2:289–303).

An effective amount of the liposome-nucleic acid complex is delivered to the subject's lung (either alveoli or airway). While there is no direct method of measuring the amount of liposome-nucleic acid complex delivered to the alveoli, bronchoalveolar lavage (BAL) can be used to indirectly measure alveolar concentrations of the expressed protein, usually 18–24 hrs after inhalation to allow clearance of the protein deposited in the larger airways and bronchi. It should also be understood that the amount of expressed protein measured in the alveoli may be substantially less than what would be expected to be expressed from the amount of nucleic acid present in the aerosol, since a large portion of the complex is exhaled by the subject or is trapped on the interior surfaces of the nebulizer apparatus. For example, approximately one third of the dose that is placed into the nebulizer remains in the nebulizer after inhalation is completed. This is true regardless of the dose size, duration of inhalation, and type of nebulizer used. Moreover, resuspension of the residue and readministration does not significantly increase the dose delivered to the subject—about one third remains in the nebulizer. Furthermore, even with minimization of airway deposition, there is a portion which is still deposited in the patient's airways. Additionally, efficiency of expression of the encoded protein will vary widely with the expression system used.

As used herein, with reference to dosages, "liposome-nucleic acid aerosol" refers to the amount of liposome-nucleic acid complex that is placed in the nebulizer and subjected to aerosolization. The "amount nebulized" or "amount aerosolized" of the complex means the amount that actually leaves the apparatus as an aerosol, i.e., the amount placed into the apparatus less the amount retained in the reservoir and on the inner surfaces of the apparatus at the conclusion of a treatment session.

The total amount of the nucleic acid delivered to the subject will depend upon many factors, including the total amount aerosolized, the type of nebulizer, the particle size, subject breathing patterns, severity of disease, concentration and the mean diameter of the liposome-nucleic acid complex in the aerosolized solution, and length of inhalation therapy. Despite these interacting factors, one of ordinary skill in the art will be able to readily design effective protocols, particularly if the particle size of the aerosol is optimized. Based on estimates of nebulizer efficiency, an effective dose delivered will usually lie in the range of about 1 mg/treatment to about 500 mg/treatment, although more or less may be found to be effective depending on the subject and desired result. It is generally desirable to administer higher doses when treating more severe conditions.

The frequency of treatments depends upon a number of factors, such as the amount of liposome-nucleic acid complex administered per dose, as well as the health and history of the subject. In general, in the treatment of cancer, it will usually be necessary to administer sequential doses at intervals ranging from every 8 to 12 hours to once a month, until significant amelioration or complete disappearance of the cancer results, or until dose limiting host toxicity develops. Similar administration protocols may also be used in i.e. patients where all macroscopic evidence of tumor has been removed, in order to prevent tumor recurrence due to persistence of undetected microscopic disease.

To treat pulmonary infections such as bronchitis and pneumonia, it will usually be necessary to administer at least one dose per day over a period of about 4 to about 21 consecutive days or longer. The treatment is usually carried out on consecutive days because new areas of the lungs open up to penetration and deposition of the nucleic acid with increasing resolution of the infection. The success of the treatment can be monitored and the administration regimen altered by assessing conventional clinical criteria; e.g., clearing of radiographic infiltrate, improved arterial $PO_2$ (e.g., >70 mmHg), reduction in dyspnea, respiratory rate and/or fever.

For the treatment of genetic disorders, such as cystic fibrosis, the liposome-nucleic acid complex will be administered at regular intervals, from once a week to once every one to several months, in order to replace the normal CRTR protein in critical host airway cells, since these cells continue to turn over. It may also be possible to stably transfect the CFTR gene into appropriate lung stem cells, which would then provide a continuous source of normal airway cells without requiring lifelong treatment.

The following examples are provided for illustrative purposes only and are not meant to limit the scope of the present invention.

C. Experimental

Example

To test whether aerosolized liposome-nucleic acid complexes could result in in vivo expression, several expression vectors, containing the chloramphenicol acetyltransferase (CAT) reporter gene, were delivered to rodent lungs. The vectors used were plasmid pRSV-CAT, as described by Gorman, et al., *Proc. Natl. Acad. Sci.* USA (1982) 79:6777–6781; and Huang, M. T. F. and Gorman, C. M., *Mol. Cell. Biol.* (1990) 10:1805–1810; a plasmid containing the CAT gene driven by the RSV long terminal repeat; and plasmid pRSV-β-gal, as described by Hazinski et al., *Am. J. Respir. Cell Mol.* Biol. (1991) 4:206–209. Also tested was a plasmid containing the CAT gene driven by the CMV promoter. This vector was made as described in Huang, M. T. F. and Gorman, C. M. *Nuc. Acids Res.* (1990) 18:937–947, with the exception that the CMV promoter was used rather than the SV40 promoter in the plasmid pML.I.CAT, described therein. Briefly, the vector was constructed by first making a pML-based plasmid containing the CMV promoter immediately followed by a portion of the 5'-untranslated leader from the adenovirus-major late (AML) region. This region contained all but the first 13 nucleotides of the first exon of the tripartite leader plus a portion of an intervening sequence (IVS) from the AML region. A synthetic oligonucleotide was inserted which merged with the adenovirus intron to provide a functional splice acceptor sequence derived from an IgG variable region. Bothwell, et al., *Cell* (1981) 24:625–637. This vector was then cut at two restriction sites bordering the intron (ClaI and PstI) to remove a 292 bp fragment. A matching synthetic oligonucleotide linker was inserted. The plasmid was termed pCMV-ICAT.

The pRSV-CAT plasmid was complexed to liposomes and administered to rodent subjects as follows. 2 mg of pRSV-CAT was mixed with 4 µmoles of DOTMA (GIBCO BRL, Grand Island, N.Y.)/cholesterol (2:1) small unilamellar liposomes in phosphate buffered saline and then nebulized in an Acorn I nebulizer (Marquest Medical Products, Inc., Inglewood, Colo.) to groups of rats or mice in an Intox nose only exposure chamber (Intox Products, Albuquerque, N.M.). The same procedure was followed with 0.5 mg pRSV-CAT mixed with 1.0 µmol DOTMA-cholesterol, as well as 2.0 mg pRSV-CAT alone. Two to five days later, animals were sacrificed and lungs collected. Lungs were also collected from untreated controls. The lungs were homogenized and cells disrupted with three freeze-thaw cycles. CAT activity in aliquots from these lung extracts was measured using a standard assay as described by Wolff, et al., *Science* (1990) 247:1465–1468. As can be seen in FIG. 1, animals administered 2.0 mg RSV-CAT with 4.0 µmol DOTMA/cholesterol expressed the CAT protein while the control animals did not.

A similar procedure was followed with respect to pRSV-β-gal, with the exception that 50 mg of pRSV-β-gal was mixed with 50 µmoles of DOTMA/cholesterol (2:1). The presence of β-gal activity was determined using a standard histochemical staining procedure. β-gal activity was present in the airway epithelial cells of exposed rats.

Figure 2:
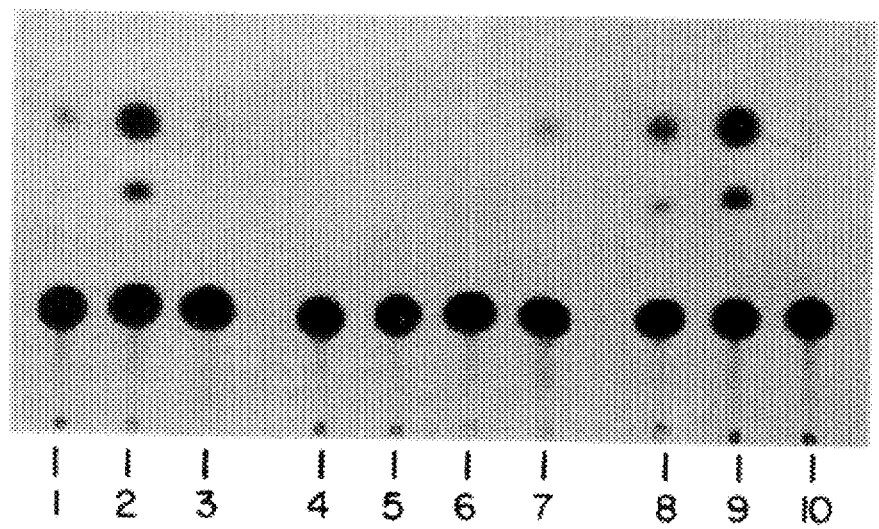
FIG. 2 shows the results of an experiment where mice were administered pCMV-ICAT complexed to DOTMA/DOPE containing liposomes. Lanes 1–3 show the results from animals administered the aerosol in an Intox designed aerosol chamber; lanes 4–7 are derived from mice exposed to the aerosol in a modified mouse cage; and lanes 8–10 show the results from animals placed in a smaller modified cage after being put in restrainers used in the Intox chamber.

To test for expression of the CAT gene using pCMV-ICAT, 12 mg of pCMV-ICAT was mixed with 12 µmoles of DOTMA/DOPE. Female ICR mice were placed in three different aerosol receiving chambers. All mice received the same amount of the CAT expression plasmid complexed to liposomes, as described above. Animals 1–3 were exposed to the aerosol in an Intox designed aerosol chamber. Animals 4–7 were exposed to the aerosol in a modified rat cage containing dividers for individual mice. Animals 8–10 were placed in a smaller, similarly modified mouse cage after being put in the restrainers used in the Intox chamber. 48 hours following aerosolization, the animals were sacrificed and whole lungs assayed for CAT expression using the chromatographic CAT assay. As can be seen in FIG. 2, animals in each group expressed the CAT gene. The amount of variation seen here is comparable to that seen in other aerosol experiments and may have several explanations, including variations in exposure to the aerosol mist, individual variations in efficiency of nasal filtration, etc.

Thus, methods of gene delivery via aerosol administration are disclosed. Although preferred embodiments of the subject invention have been described in some detail, it is understood that obvious variations can be made without departing from the spirit and the scope of the invention as defined by the appended claims.

I claim:

1. A method of introducing a DNA molecule into a cell of the proximal or distal airways of a mammal, which DNA molecule comprises expression regulatory elements operatively linked to a nucleotide sequence to be expressed in said cells, the steps of the method comprising administering an aerosolized composition comprising the lipid-DNA complex to the nasal or oral passages of the mammal, wherein the composition comprising the lipid-DNA complex is substantially free of macroaggregates, and whereby the lipid-DNA complex contacts the airway of the mammal and the DNA molecule is introduced into a cell of the airway, and the nucleotide sequence is expressed in the cell.

2. The method of claim 1, wherein the DNA molecule is introduced into a lung cell in the lung of the mammal.

3. The method of claim 1, wherein the cationic lipid comprises a cationic lipid selected from the group consisting of DOTMA, DDAB, and DOTAP.

4. The method of claim 1, wherein the cationic lipid-DNA complex further comprises cholesterol.

5. The method of claim 4, wherein the cationic lipid and cholesterol are in a mass ratio of about 2:1.

6. The method of claim 1, wherein the cationic lipid-DNA complex further comprises DOPE.

7. The method of claim 1, wherein the cationic lipid-DNA complex further comprises a neutral or anionic lipid.

8. The method of claim 1, wherein the cationic lipid-DNA complex further comprises a non-cationic lipid selected from the group consisting of phosphatidyl choline, cholesterol, phosphatidyl ethanolamine, dioleoylphosphatidyl choline, dioleoylphosphatidyl glycerol, and, dioleoylphosphatidyl ethanolamine.

9. The method of claim 1, the complex prepared from an MLV, an LUV, or an SUV.

10. The method of claim 1, wherein the complex comprises DNA and cationic lipid components in a ratio of about 1 mg DNA:1 micromole cationic lipid.

11. The method of claim 1, wherein the complex is administered in a pharmaceutically acceptable excipient.

12. The method of claim 1, wherein the complex is substantially free of chelating agents.

13. The method of claim 1, wherein the complex is aerosolized in a nebulizer.

14. The method of claim 1, wherein the cationic lipid-DNA complex in aerosol form has a mean particle diameter of less than about 15 µm.

15. The method of claim 1, wherein the cationic lipid-DNA complex in aerosol form has a mean particle diameter of less than about 5 µm.

16. The method of claim 1, wherein the cationic lipid-DNA complex in aerosol form has a mean particle diameter of less than 2 µm.

17. The method of claim 1, wherein the cationic lipid-DNA complex comprises a nucleic acid base analog.

18. The method of claim 1, wherein the mammal is a mouse.

19. The method of claim 1 wherein expression of the nucleotide sequence results in production of a polypeptide encoded by the nucleotide sequence.

20. The method of claim 1, wherein the mammal has a disease selected from the group consisting of: lung cancer, emphysema, asthma, bronchitis, pneumonia, cystic fibrosis and α-1 antitrypsin deficiency.

21. The method of claim 1 wherein the expression regulatory elements include a promoter selected from the group consisting of: an SV40 promoter, a CMV promoter, an HSV promoter, an RSV promoter, an MMTV promoter, a T7 promoter, and a T3 promoter.

22. The method of claim 1, wherein the complex comprises a DNA encoding a protein, which DNA comprises a promoter sequence which regulates transcription of an mRNA encoding the protein in a host cell in the mammal, wherein the protein comprises a secretory signal.

23. The method of claim 1, further comprising repeated administration of the complex in aerosol form to the mammal.

24. The method of claim 1, further comprising repeated administration of the complex in aerosol form to the mammal for between about 4 and about 20 days.

25. The method of claim 1, wherein the delivery of the complex to the lung provides for the transduction of cells in the lung, thereby making transformed cells, the method further comprising repeated administration of the complex in aerosol form to the mammal to replace transformed cells lost to natural turn over of lung cells.

* * * * *

UNITED STATES PATENT AND TRADEMARK OFFICE
CERTIFICATE OF CORRECTION

PATENT NO. : 5,756,353
DATED : May 26, 1998
INVENTOR(S) : Roger J. Debs

It is certified that error appears in the above-identified patent and that said Letters Patent is hereby corrected as shown below:

On the title page, item 56, 5,676,954  10/14/97  Brigham ............ 424/450

Signed and Sealed this

First Day of September, 1998

Attest:

BRUCE LEHMAN

Attesting Officer

Commissioner of Patents and Trademarks